United States Patent [19]
Greco et al.

[11] Patent Number: 5,352,194
[45] Date of Patent: Oct. 4, 1994

[54] AUTOMATED DEVICE FOR LIPOSUCTION

[75] Inventors: Richard J. Greco; Mark B. Freidman; J. William Futrell, all of Pittsburgh, Pa.

[73] Assignee: University of Pittsburgh, Pittsburgh, Pa.

[21] Appl. No.: 905,726

[22] Filed: Jun. 29, 1992

[51] Int. Cl.$^5$ .............................................. A61B 17/00
[52] U.S. Cl. ..................................... 604/35; 604/65; 604/95; 604/121; 604/156; 604/174; 604/902; 128/766
[58] Field of Search ............... 128/632, 752, 758, 766; 604/22, 27, 31, 35, 43, 65, 95, 102, 119, 121, 156, 157, 158–165, 174, 152, 902

[56] References Cited

U.S. PATENT DOCUMENTS

| | | | |
|---|---|---|---|
| 2,936,760 | 5/1960 | Gants | 604/102 |
| 3,459,175 | 8/1969 | Miller | 604/174 |
| 4,077,412 | 3/1978 | Moossun | 604/174 |
| 4,168,707 | 9/1979 | Douvas et al. | 604/31 |
| 4,356,823 | 11/1982 | Jackson | 604/902 |
| 4,705,038 | 11/1987 | Sjostrom et al. | |
| 4,735,604 | 4/1988 | Watmough et al. | |
| 4,735,605 | 4/1988 | Swartz | |
| 4,770,187 | 9/1988 | Lash et al. | 604/404 |
| 4,792,327 | 12/1988 | Swartz | |
| 4,838,281 | 6/1989 | Rogers et al. | 604/65 |
| 4,878,901 | 11/1989 | Sachse | 604/102 |
| 4,886,491 | 12/1989 | Parisi et al. | 604/902 |
| 4,986,827 | 1/1991 | Akkas et al. | 606/107 |
| 5,000,191 | 3/1991 | Reiss et al. | 604/902 |
| 5,076,787 | 12/1991 | Overmyer | 604/902 |
| 5,122,122 | 6/1992 | Allgood | 604/174 |
| 5,122,302 | 5/1992 | Cucin | 604/902 |
| 5,147,316 | 9/1992 | Castillenti | 604/164 |

FOREIGN PATENT DOCUMENTS

| | | | |
|---|---|---|---|
| 2622457 | 5/1989 | France | 604/157 |
| 2648050 | 12/1990 | France | 604/902 |
| 1255140 | 9/1986 | U.S.S.R. | 604/157 |

Primary Examiner—Stephen C. Pellegrino
Assistant Examiner—Jeffery A. Schmidt
Attorney, Agent, or Firm—Reed Smith Shaw & McClay

[57] ABSTRACT

The present invention provides a device for performing suction lipectomy or liposuction in which the reciprocal motion required during the liposuction procedure is automated. This automation greatly reduces the physical exertion required of the operating surgeon. The present invention also allows the use of smaller cannulae to achieve an improved aesthetic result. Use of such smaller cannulae with the manual liposuction procedures currently in use would be extremely taxing if not impossible.

63 Claims, 11 Drawing Sheets

AUTOMATED DEVICE FOR LIPOSUCTION

FIELD OF THE INVENTION

The present invention relates to a device for removal of unwanted fat tissue, and more particularly, to an automated lipectomy device.

BACKGROUND OF THE INVENTION

Aesthetic body contour surgery has become a routine procedure by which to increase the attractiveness of the human form. One particular method of body contour surgery, suction lipectomy or liposuction, is a procedure that permits elimination of localized fat deposits through small incisions which leave inconspicuous scars. Liposuction is one of the most common aesthetic procedures performed by plastic and reconstructive surgeons today.

Liposuction has been used to remove fat from many regions of the body. The regions most frequently treated include the trochanteric region, flanks, buttocks, interaspect of the knee, the anterior abdominal wall, gynecomastia, and "love handles." Although it was once believed that the fat cells removed by liposuction would later be replaced, the presently accepted theory is that the body contains a limited number of fat cells which cannot regenerate. Fatty tissue is not caused by an increase in the number of fat cells, but by an increase in the amount of lipid matter found within the cell. Therefore, the removal of fat cells by liposuction should create a contour that will retain its form (absent undue expansion of lipid matter in remaining cells).

Liposuction was first performed in Europe by J. Schrudde in 1972 using a uterine curette. Currently, the procedure is performed using a special type of curette known as a cannula. The cannula is attached to a vacuum source which carries away the fat tissue. The vacuum required is inversely proportional to the size of the suction aperture and the tube diameter (i.e., the smaller the tube and the orifice, the higher the negative pressure needed for the evacuation of the fat). The vacuum pressure in one often used cannula, known as the Aspiradeps, manufactured by Ulrich A. G., in St. Gall, Switzerland, is usually on the order of 0.4 to 0.6 atmospheres.

There are theoretically two different methods by which to remove fat through liposuction. The first of these methods is the tunneling procedure as proposed by Y.-G. Illouz. In the Illouz method, one or two incisions are made. Radial excursions of the instrument into the flesh via the incisions are then made. The result is a multitude of concomitant sinuses. The second method is the original liposuction procedure as proposed by U.K. Kesserling. In the second technique, an entire layer of regular, deep fat is removed, leaving a smooth, deep surface of residual panniculus. The space created is then transformed by compression into a virtual space in which primary healing can take place. Optimally, skin retractions may follow.

Both of the above techniques require the surgeon to push and pull a portion of the cannula back and forth multiple times for each tunnel made. Generally, twenty to thirty tunnels per incision are made to insure even removal of fat in the targeted regions. The surgeon typically massages the flesh in the area of the aperture in the cannula, while at the same time thrusting the rod in and out of the tunnel. This method is extremely traumatic, both for the patient and the doctor. The patient's flesh turns black and blue for several days. Moreover, many surgeons practicing liposuction find it physically exacting, and most come out of the operating room extremely tired after procedures in which large areas are liposuctioned.

It is known from the clinical experience and the work of Kesserling, Illouz, E. H. Courtiss, R. A. Mladick and others, that the sense of aesthetics, symmetry and the amount of trauma human tissue can tolerate must be controlled and guided by an experienced operator and cannot be replaced with currently available machines. Furthermore, clinical observations have led to the opinion that the use of small cannulae leads to less contour deformity and less skin dimpling. Others have felt that the fatigue factor may subtly influence a surgeon's opinion regarding whether he has removed enough fat, while objectively, he would need to continue the process. Automation of the liposuction procedure is, therefore, desirable. Development of an automated liposuction device is therefore desirable.

Several, automated or assisted surgical instruments are currently available for removing biological material. In U.S. Pat. No. 4,735,605 and U.S. Pat. No. 4,792,327, issued to B. E. Swartz, for example, an improved cannula is disclosed. The cannula comprises an outer tube with an elongated aspiration aperture and an inner tube with a spiral slot. A mechanism inside the handle of the device causes the inner tube to rotate, creating a "traveling hole effect" along the elongated aspiration aperture. The "traveling hole effect" is intended to obviate the need to repeatedly push the cannula in and out.

A mechanical apparatus for removing biological material is also disclosed in U.S. Pat. No. 4,735,604 issued to Watmough, et al. Watmough, et al. discloses a device comprising a hollow tubular elongated member mounted for longitudinal sliding movement in a casting. The casting includes a rotatable drive shaft which causes the tubular member, the distal end of which is adapted for removal of biological material, to vibrate at relatively low amplitude and high frequency. The biological material is withdrawn via the tubular member using a negative pressure gradient.

In U.S. Pat. No. 4,705,038 issued to Sjostrom, et al., a single-motor surgical system for operating a set of different surgical devices having different operational limits is disclosed. The system includes a handpiece containing a motor adapted to alternatively receive a proximal portion of several surgical devices, each device provided with an indicator in its proximal portion denoting its operational limits. The handpiece includes an automatic sensor for controlling the motor in accordance with the indicated operational limits of the surgical device currently connected to the handpiece. Each of the plurality of surgical devices preferably includes a vacuum passage adjacent a connectable rotary tip, whereby tissue severed by the rotary tip can be removed from the surgical site.

Automated surgical devices currently available, however, fall far short of providing reliable controlled mechanization of the reciprocal motion required for patient safety and aesthetically pleasing liposuction results. It is therefore desirable and advantageous to develop a device which would safely automate the motion of the cannula to assist the surgeon in the lipectomy procedure by decreasing the physical exertion expended by the surgeon. A device that allows effortless liposuction with a small cannula would allow the surgeon to remove more fat, in a more symmetric and even fashion, and yield an improved aesthetic resulted. The use of smaller cannulae will also reduce trauma to the patient.

SUMMARY OF THE INVENTION

Accordingly, the present invention provides a device for performing liposuction in which the required rectilinear, reciprocal motion of the cannula is mechanically automated. Generally, the present device comprises a handle means, a powered means for producing a controlled, rectilinear, reciprocal motion of the cannula of a stroke length of at least 1 cm, and a means for operatively connecting a cannula to the powered means.

By automation of the reciprocal motion required during liposuction, the present device allows liposuction with minimum effort on the part of the surgeon, with smaller cannulae than presently used. Use of such small cannulae over large areas is almost physically impossible under the present manual procedures. Older, more experienced surgeons will be able to continue this operation when the manual procedures currently in use would have been too physically taxing for them. Furthermore, less skin dimpling and better body contour can be obtained with the use of only small cannulae.

DESCRIPTION OF THE PREFERRED EMBODIMENTS

Figure 1:
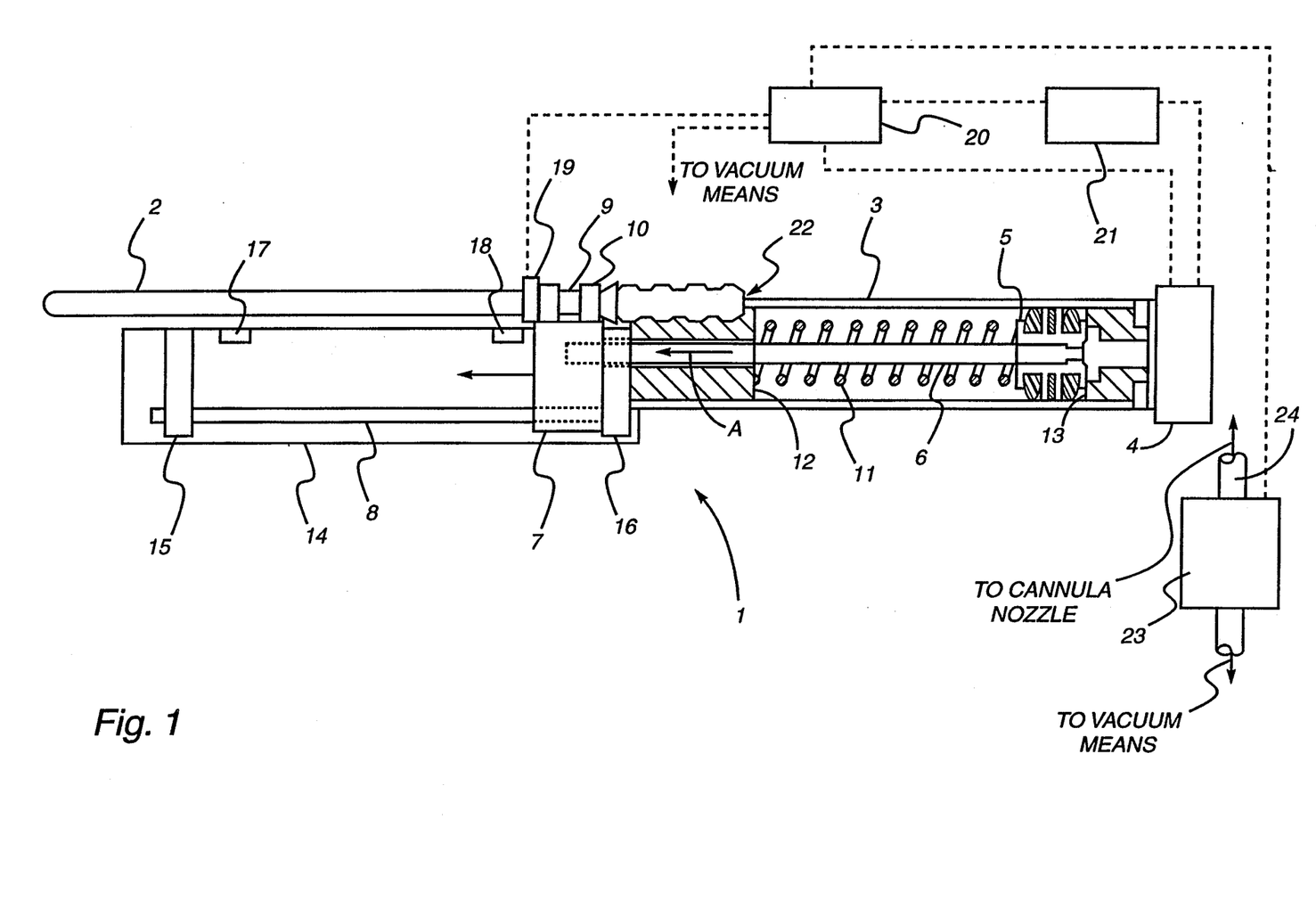
FIG. 1 is a top view of an embodiment of the present invention showing a single-acting pneumatic cylinder in cross-section.

With reference to FIG. 1, a top view of a device 1 for performing suction lipectomy or liposuction in accordance with the present invention is shown. The surgeon performing the liposuction procedure holds device 1 and controls the direction of the motion of cannula 2 via a handle means 3 as depicted in FIG. 1. During operation cannula 2 is operatively attached to a means for producing the reciprocal motion via appropriate attachment means. Generally, cannulae currently in use can be used with the present invention.

The controlled, reciprocating motion of a liposuction cannula can be generated via mechanical, electric, hydraulic or pneumatic power. Electric power has the advantage of ease of electronic control. If the cannula motion is produced with lead screws or highly geared drive chain/cable systems powered by small rotary motors, sensors and control electronics must be incorporated into the drive system to control cannula forces in a fail-safe manner. The forces generated by linear motors are somewhat easier to directly limit in the necessary, fail-safe manner, but small, lightweight linear actuators having the required range of motion and force are relatively expensive, both to purchase and to control. Both linear and conventional rotary motor systems require care in electrically isolating the cannula (which is in intimate contact with the patient's tissue during operation) from the drive and sensor electronics.

Hydraulic rotary and linear actuators can more easily provide the requisite level of electronic isolation from the cannula. However, force sensors are required to ensure the the mechanical compliance necessary to guarantee controlled, low cannula tip forces. Small diameter, lightweight hydraulic piston actuators may not be readily available in the "throw" or "stroke" lengths required for liposuction.

Pneumatic cylinders are the preferred alternative for powering the reciprocating cannula motion needed for a liposuction power hand tool. Such cylinders provide the mechanical compliance to enable control of cannula force without the use of force sensors. The mechanical compliance of pneumatic cylinders is directly proportional to the volume of the cylinder used. Moreover, extremely compact, lightweight cylinders are commercially available in the size and force ranges that are required. The cylinders are also available in materials compatible with normal sterilization procedures. Medically approved, affordable pressure regulators exist to limit the tool's applied forces in a fail-safe manner. Further, filtered compressed air sources of the required pressure and volume are readily available in most surgical operating rooms. The pneumatic systems proposed in this invention can also be powered from readily available cylinders containing compressed nitrogen or carbon dioxide. Since a portable, high volume vacuum system is a principal component of current commercial liposuction apparati, little additional noise would be introduced by the use of an air compressor to power the present invention in facilities without compressed air sources.

Either single-acting, spring return cylinders or a double-acting pneumatic cylinders can be used. In the case of a single-acting cylinder, the forward stroke is effected via pneumatic pressure, while the force for the reverse or return stroke is provided by a spring. A single-acting cylinder may also function in the reverse manner. In the case of a double-acting cylinder, both the forward and reverse strokes are pneumatic powered.

The spring-powered retraction of the single-acting cylinders can be considered safer under some controlled failure modes. In case of a power failure, for example, a single-acting cylinder in which the return stroke is spring-powered will always be fully retracted. The high reliability and motion control offered by double action makes the double-acting cylinder preferable in situations where accurate control of cannula motion is required in both the forward and reverse stroke.

Referring again to FIG. 1, a preferred embodiment of the present invention incorporating a single-acting pneumatic cylinder 3 is shown. Cylinder 3 is shown in cross-section. In this embodiment, cylinder 3 also serves as the handle means by which the operating surgeon grips the device.

During operation, compressed air or another appropriate gas is supplied to three-way valve 4 to drive piston 5 in the forward direction (indicated by arrow A). Valve 4 can also be remote to cylinder 3. Rod 6, which is firmly attached to piston 5, moves forward driving guide plate 7 forward along guide rod 8 upon which guide plate 7 is slideably disposed. Cannula 2, which is firmly attached to guide plate 7 via cannula attachment means 9 and 10, is thereby driven forward. Upon reaching the desired stroke length, the compressed gas is vented from cylinder 3 via valve 4. Upon the resultant decrease in pressure, the force exerted by spring 11 returns piston 5 to its retracted position. Repeating this sequence of events results in the reciprocating motion required during liposuction.

Various aspects of the cannula motion can be controlled during liposuction, while others can be preset or deferred until a pause in the operative procedure. The liposuction cannula motion variables of interest include stroke length, force, rate (strokes/time), and symmetry of motion.

Several alternative means are available for controlling the stroke length of cannula 2. Preferably, more than one such stroke length control means are in place in the system to ensure safe operation. Pneumatic cylinder 3 has an inherent limiting stroke length. As seen in FIG. 1, cylinder 3 is provided with internal abutment means 12 and 13 which limit the forward and reverse motion of piston 5, respectively. In FIG. 1, piston 5 is shown in its completely retracted position resting against abutment means 13. It is also possible to provide mechanical abutment means for limiting the stroke length external to the cylinder 3. In FIG. 1, for example, device 1 is provided with an external support base 14. Attached to support base 14 are external abutment means 15 and 16. External abutment means 15 and 16 may be made adjustable along the length of base 14. Mechanical abutment means provide a fail safe manner of limiting the maximum stroke length.

Preferably other means of controlling the stroke length are also provided. In FIG. 1, switches 17 and 18 are shown attached to support base 14. Switches 17 and 18 may be, for example, electromechanical, electro-optical or electromagnetic in operation. Switches 17 and 18 are used to control valve 4 to provide the reciprocal cannula motion as described above. The position of switches 17 and 18 is preferably made adjustable to produce a variety of stroke lengths. In the embodiment shown in FIG. 1, switches 17 and 18 operate to sense the position of guide plate 7 and control the motion of cannula 2 via control of valve 4 in the appropriate manner. External abutment means 15 and 16 can be adjusted to correspond in location with switches 17 and 18 to ensure that the desired stroke length is not exceeded.

Figure 2:
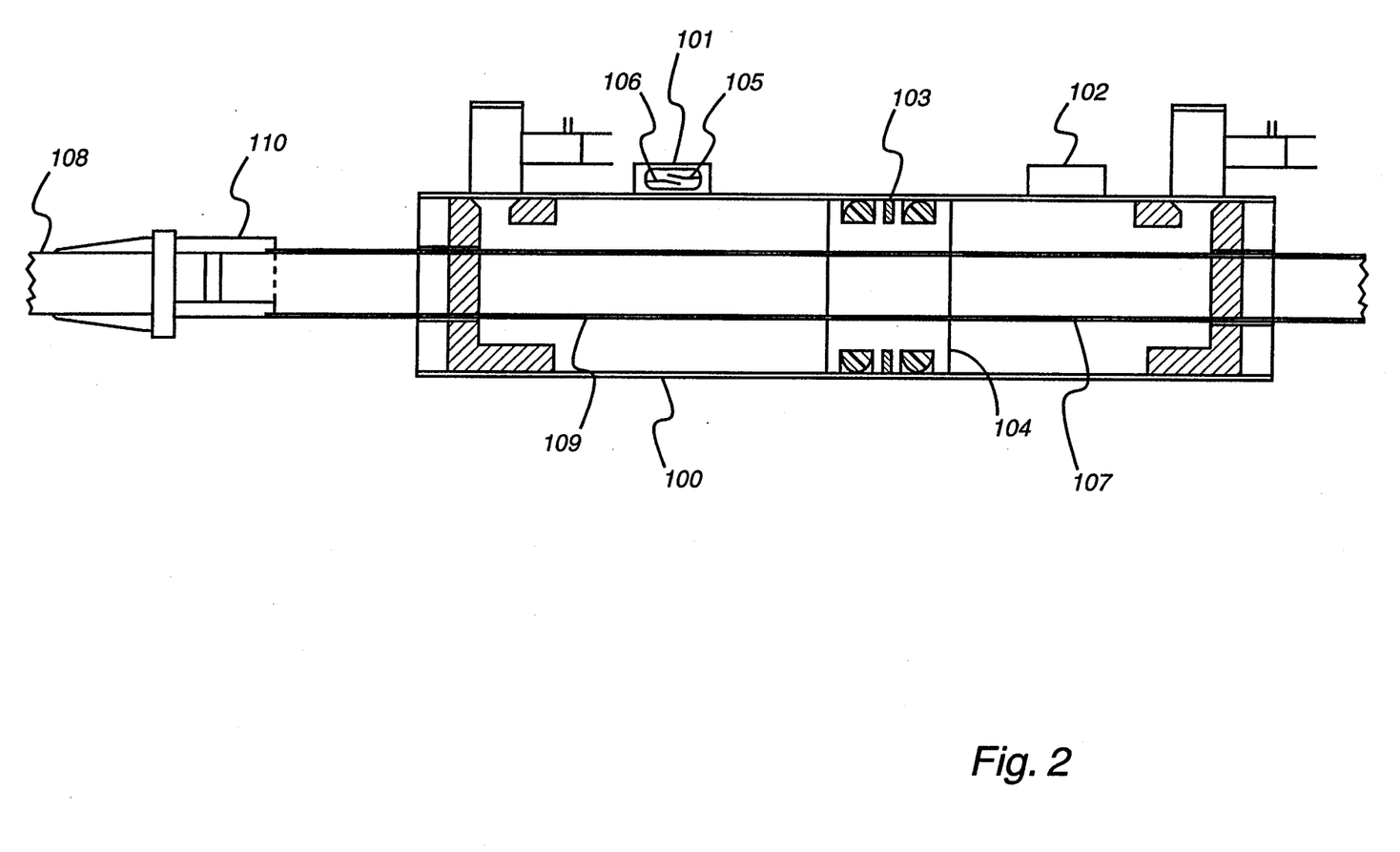
FIG. 2 is a side view of an embodiment of the present invention showing a double-acting pneumatic cylinder in cross-section.

Switches may also be placed upon the cylinder itself to control stroke length. In FIG. 2, for example, a double-acting pneumatic cylinder 100 is illustrated upon which magnetic reed switches 101 and 102 are mounted. Such switches are available from Bimba Manufacturing Company, Monee, Ill. 60449-0068. In the use of magnetic reed switches 101 and 102, a magnet 103 is mounted on piston 104. Magnetic reed switch 101 is shown in cross-section. When magnet 103 of piston 104 travels in the proximity of one of magnetic reed switches 101 or 102 the normally open contacts 105 and 106 will close or "pull in." When the magnet travels away from the switch, the contacts will open or "drop out."

Referring to FIG. 1, the force exerted upon piston 5 and thus the force, rate and symmetry of motion of cannula 2 can be controlled by adjusting the rate of inflow of gas on the forward stroke and adjusting the rate of exhaust of the gas on the reverse stroke (e.g., through use of a needle valve). Valve 4 is preferably a servovalve so that active control can be maintained over the motion of cannula 2.

Also, device 1 preferably includes a means 19 for sensing the force being applied to cannula 2. Sensor 19 can be, among other types of sensing devices, a cantilevered sensor, a strain gauge or a load cell. By detecting the axial force on cannula 2, the operator can be signaled or warned when such force exceeds a threshold level. A "shut-off" threshold can be established at which the pressurized gas in cylinder 3 is exhausted, cannula 2 is retracted and device 1 is shut off. Sensor 19 can also be a displacement sensor as the rate of cannula 2 is proportional to the force.

Alternately, the force being applied to cannula 2 can be measured indirectly from the pressure within cylinder 3 which is directly proportional to the cannula force. This can be accomplished using a pressure transducer (not shown). The pressure can be monitored and compared to a previously calculated pressure profile derived from existing data. If the actual pressure deviates significantly from the calculated pressure, it is likely that cannula 2 has contacted an obstacle. As with direct measurement of cannula force, threshold values of pressure can be established to ensure safe operation.

To provide feedback control of cannula variables, device 1 is also preferably provided with a microprocessing unit 20. Microprocessing unit 20 can be remote to device 1 or attached to cylinder 3 or other handle means.

Figure 3:
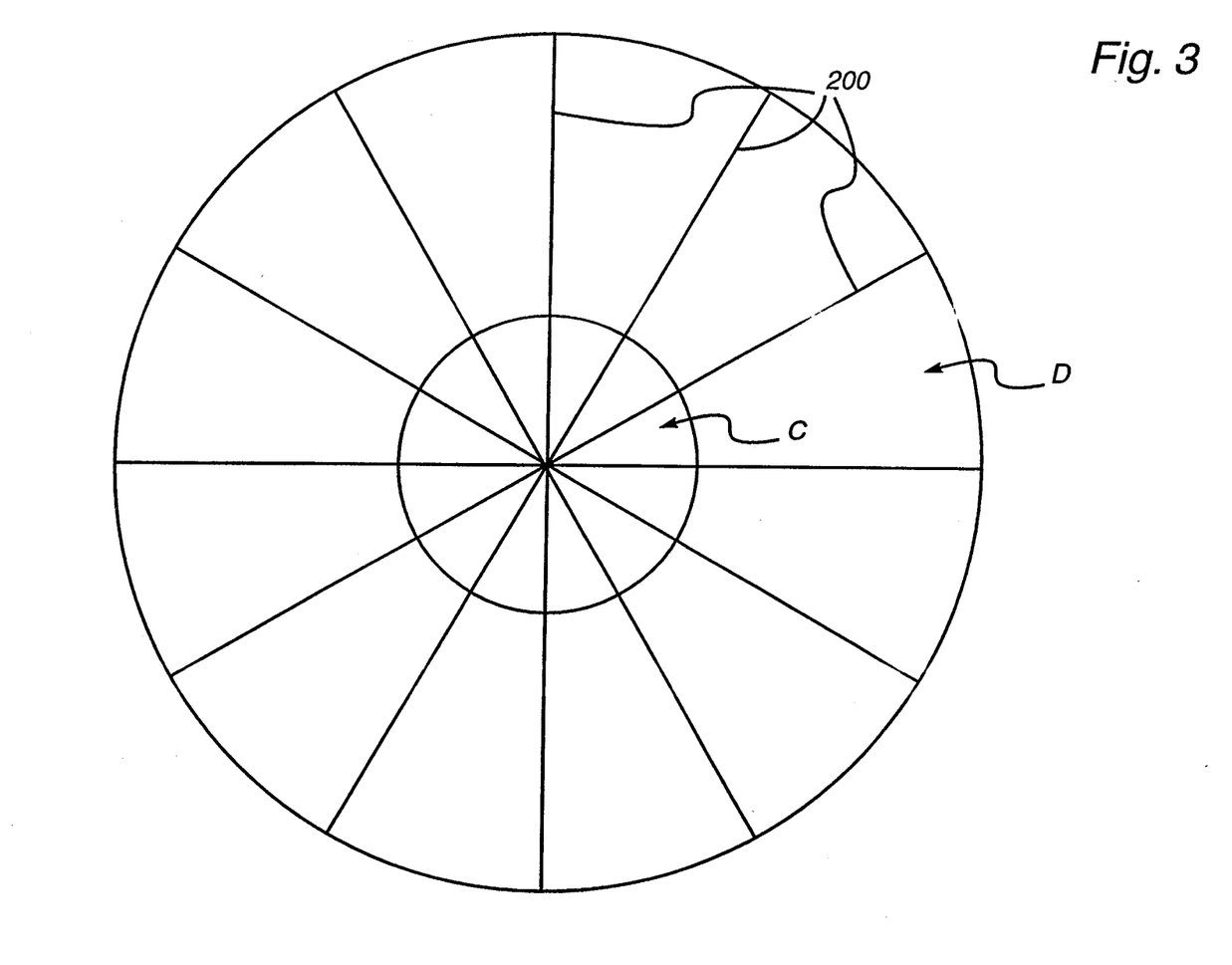
FIG. 3 is an illustration of a typical radial pattern of cannula excursion.

Using active control, the possibilities for controlling the manner of cannula excursion are almost limitless. In FIG. 3, for example, is shown a typical radial pattern of cannula excursion. Because of the close proximity of the cannula paths in a central aspect or area C of the pattern as compared to distal aspect D, a greater percentage of fat will be removed from central aspect C than from distal aspect D for any given, constant cannula rate. Assuming constant negative (vacuum) pressure, the amount of fat removed from any given area is proportional to the residence time of the cannula in that area. By moving the cannula quickly through central aspect C of the pattern and more slowly through distal aspect D, therefore, one may remove a more even distribution of fat over the entire radial pattern.

Cannula motion can be controlled in a number of ways including the mounting of multiple switches either upon cylinder 3 or upon external support base 14. Preferably, cannula 2 is controlled by modulation of servo valve 4 by a modulating means 21. Modulating means 21 can be, for example, an electronic signal generator or a waveform generator. By appropriate control of valve 4, one can produce an almost infinite variation in cannula strokes, such as sinusoidal, ramp (asymmetric triangular), trapezoidal or triangular wave. Furthermore, different waveforms can be superimposed to create additional variations.

Figure 4:
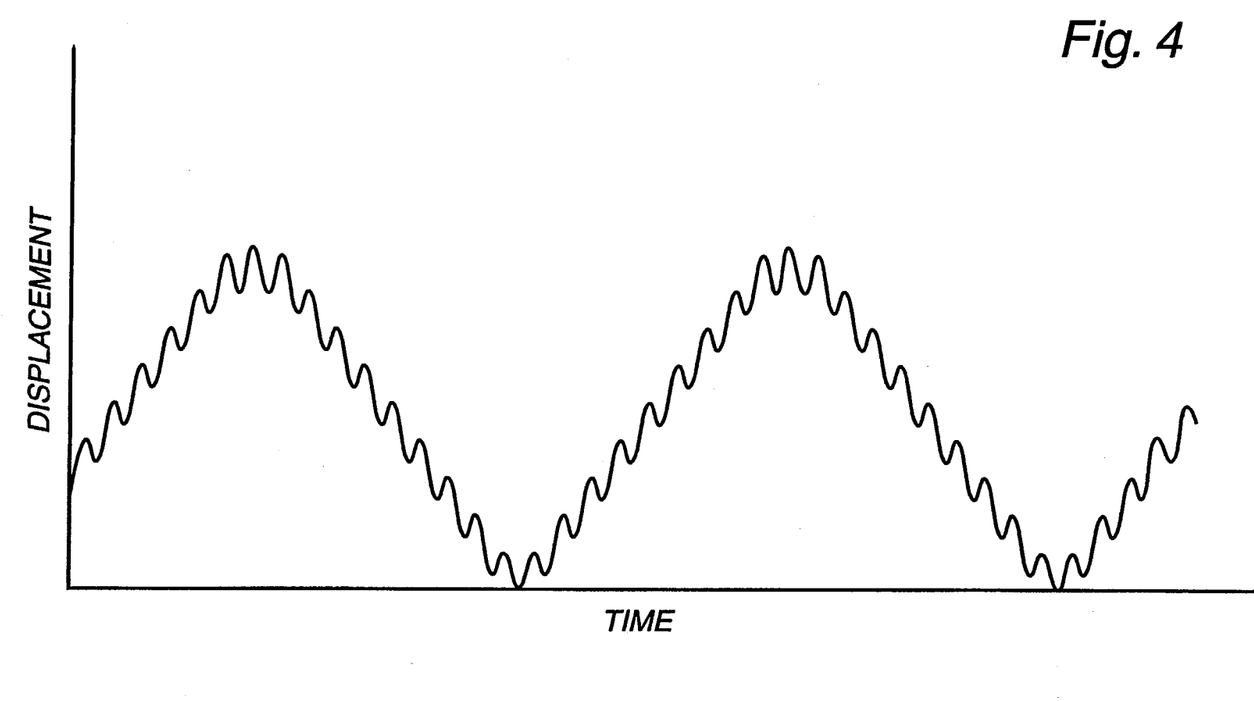
FIG. 4 is a graphical illustration of a control signal for a desired cannula motion.

In FIG. 4, for example, a high-frequency/low-amplitude wave is shown superimposed (i.e., a linear addition of two wave forms) upon a lower frequency/high-amplitude wave. A wave or function generator such as a WAVETEK Model 273 can be used. This signal would result in a substantially sinusoidal cannula stroke during which the cannula would "vibrate" at the frequency of the high-frequency/low-amplitude wave. Such cannula motion may assist in the removal of lipid material by mechanically dislodging the lipid material subjected to the vibrational motion.

By adjustment of appropriate parameters, the operating physician can thus maintain control over cannula motion that until the present invention was not possible. The automation provided by device 1 enables experimentation with cannula motion previously impossible to optimize liposuction technique to reduce both patient trauma and physician fatigue as well as to improve the aesthetic results. Preferably, controls (not shown) are mounted directly on device 1 to control cannula variables. Alternately, such controls may be remote to device 1 or incorporated into foot controls.

The means for producing the reciprocal, rectilinear motion, the handle and ultimately a cannula can be attached in the present invention in several different manners. As shown in FIG. 1, for example, they can be attached so that when the cannula is parallel but not colinear with the handle. Alternatively, a concentric tube embodiment, in which the handle and cannulae are colinear, can be used as shown in FIG. 2. Still further, the handle can be attached so as to be perpendicular to the plane of the cannula in a "gun-shaped" embodiment (not shown).

In the concentric tube embodiment shown in FIG. 2, pneumatic cylinder 100 is provided with a rod 107 which is hollow. It is possible to attach cannula 108 directly to hollow rod 107. Preferably, however, the device is provided with an inner tube 109 having an appropriate diameter to be placed within rod 107 in a concentric manner. Inner tube 109 and rod 107 are then preferably securely attached to cannula attachment means 110. Upon attachment of cannula 108–109, rod 107, inner rod 109 and cannula 108 move with the reciprocating motion of piston 104 to which rod 107 is securely attached.

The concentric tube embodiment illustrated in FIG. 2 is preferably provided with inner rod 109 to facilitate cleaning and sterilization. It is undesirable to allow biological material to directly contact rod 107. Most preferably, inner tube 109 is made disposable.

In the embodiment illustrated in FIG. 1, a vacuum means (not shown) such as a vacuum pump is preferably connected to cannula 2 at nozzle 22 via expandable, flexible tubing (not shown). In the concentric tube embodiment of FIG. 2, a vacuum means (not shown) is preferably connected to the distal end of inner tube 109 via expandable flexible tubing (not shown).

Figure 5:
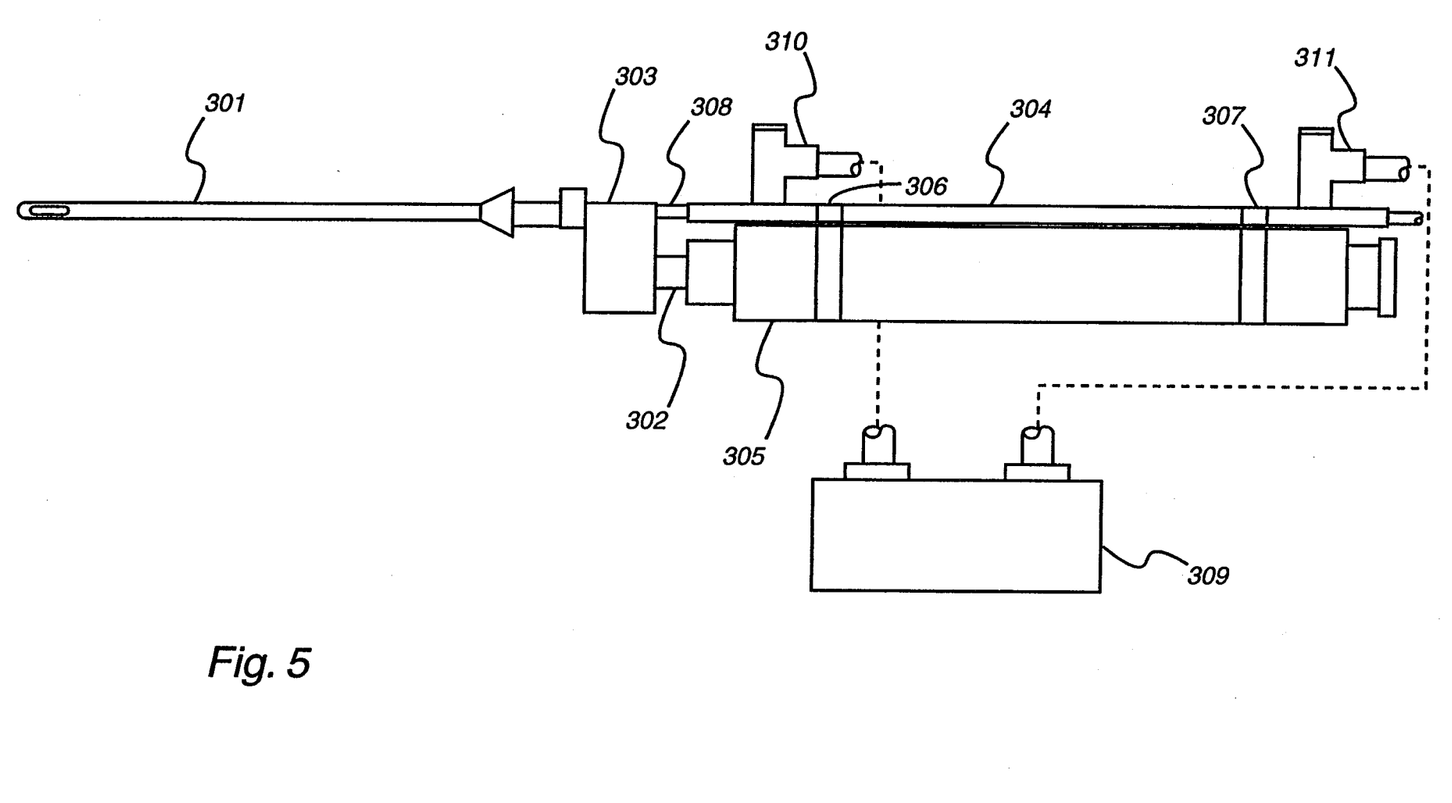
FIG. 5 is a side view of an embodiment of the present invention showing a double-acting cylinder in which the cannula is attached in a noncolinear manner.
Figure 6:
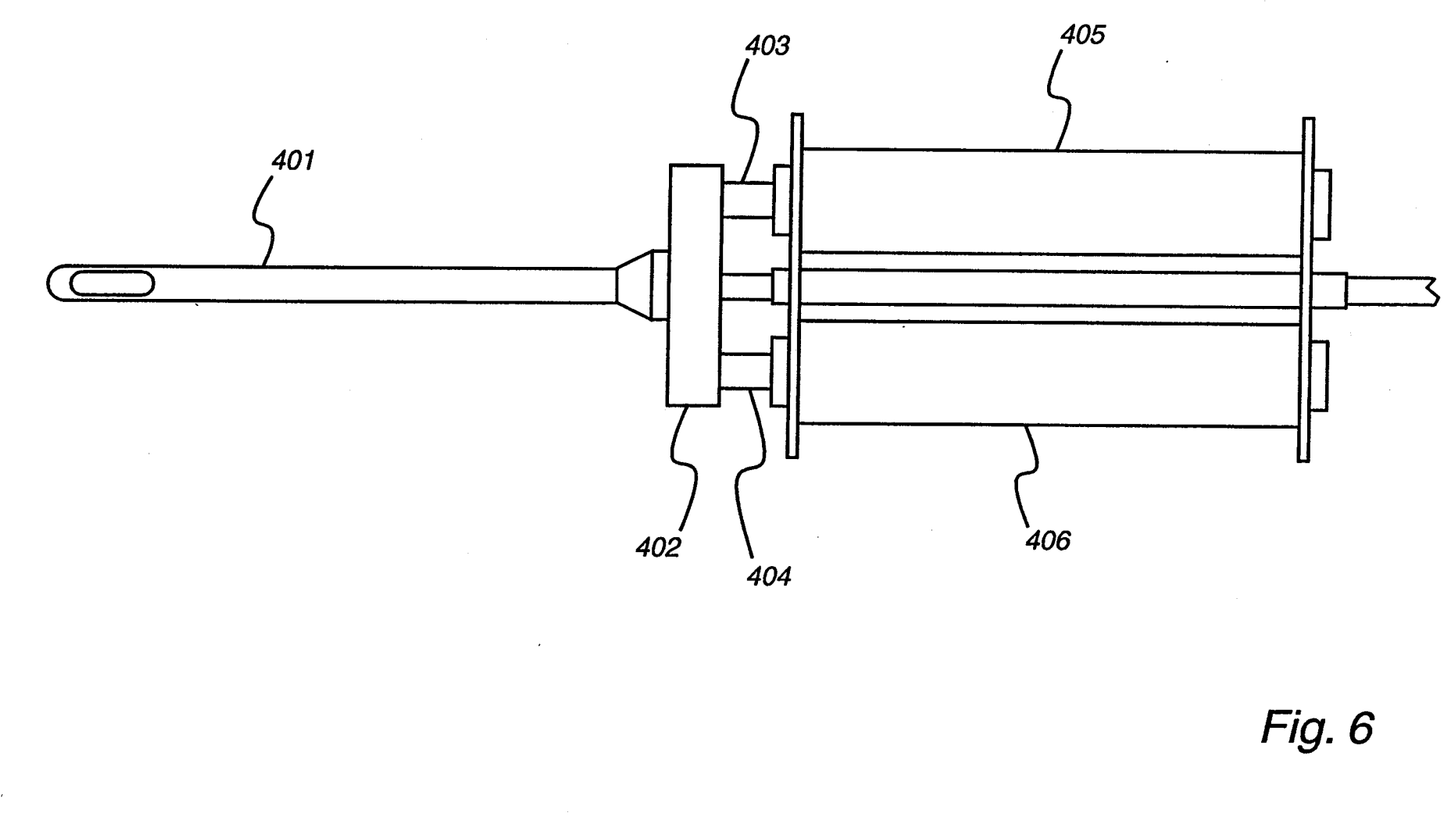
FIG. 6 is a top view of an embodiment of the present invention in which the cannula motion is powered by two pneumatic cylinders.

Depending on the design of the cannula used with the present invention, it may be desired to substantially restrict rotational motion of the cannula tangential to the axis of its rectilinear motion. It is, for example, desirable to prevent removal of lipid material too near the skin surface as dimpling may result. One may thus wish to prevent the cannula apperture from facing upwards. One can restrict rotation of the cannula in several alternative manners. First, as indicated above, the cannula can be attached to be noncolinear with the cannula rod and a guide means can be used. Nonlinear embodiments are illustrated in FIGS. 1, 5 and 6. In FIG. 1, rotation of rod 6 is prevented by its attachment to guide block 7 which is slideably disposed upon guide rod 8.

In FIG. 5, cannula 301 is attached in a nonlinear manner to rod 302 via cannula attachment means 303. The embodiment shown in FIG. 4 is also provided with external guide tube 304 which can be firmly attached to cylinder 305 via attachment means 306 and 307. A disposable inner tube 308 is attached to cannula attachment means 303 so as to slide within external guide tube 304 during the reciprocal motion of cannula 301. Therefore, biological materials come in contact only with cannula 301 and disposable tube 308.

Rotation of the cannula can further be prevented by using multiple cylinders to drive the cannula. In FIG. 6, a multi-cylinder embodiment is shown in which cannula 401 is attached to guide plate 402. Rods 403 and 404 of cylinders 405 and 406 are also attached to guide plate 402. Both cylinders 405 and 406 are operated under the same pressure profile to drive guide plate 402 and thereby cannula 401 in a controlled manner.

Figure 2A:
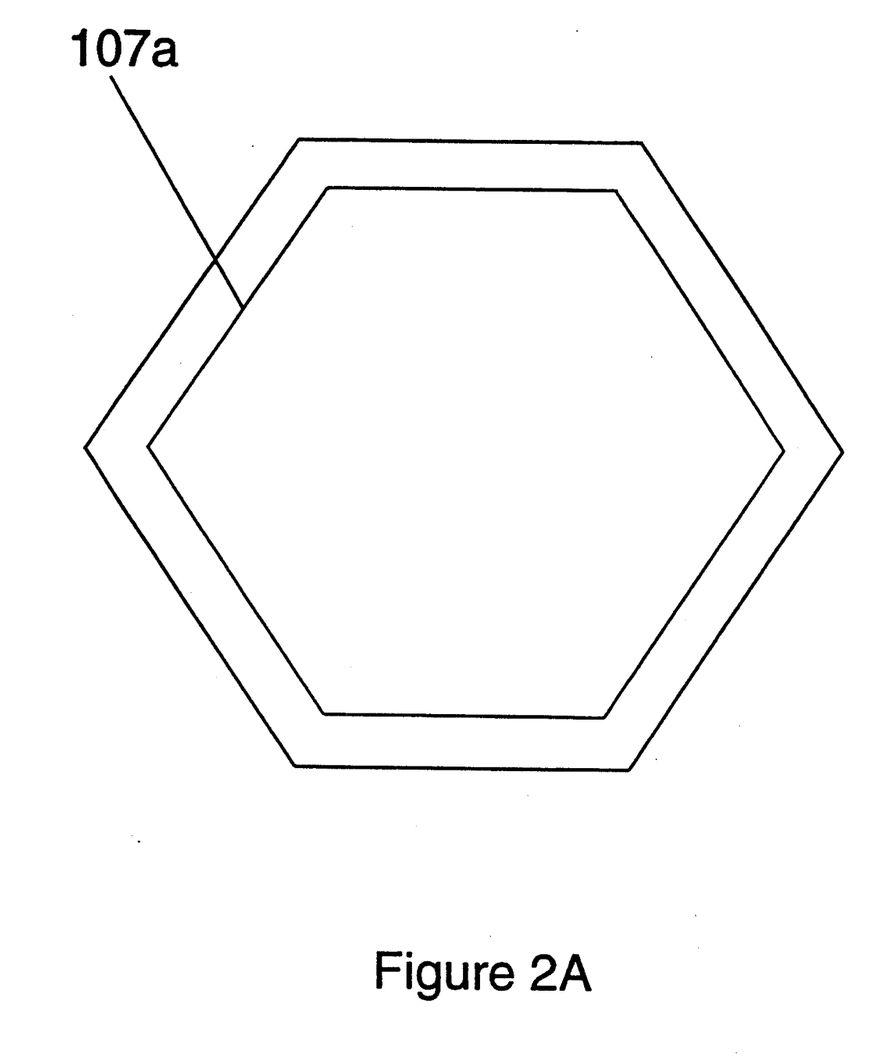
FIG. 2A is a front view of a hexagonal rod used to prevent cannula rotation.

Rotation of the cannula can also be prevented, even in a colinear embodiment as described in FIG. 2, by designing rod 107 to prevent rotation. One way to prevent rod rotation is to use a key and key-way design. Use of rods having noncylindrical outer shells will also prevent rotation. In FIG. 2A, an embodiment of a hexagonal rod 107a is illustrated. Cylinders designed to use hexagonal rods, for example, are readily available from Bimba Manufacturing Company.

Referring again to FIG. 5, a vacuum means (not shown) is attached to the distal end of inner tube 308 via flexible tubing (not shown). In addition to assisting in the prevention of tangential rotation of the cannula, the use of guide tube 304 and inner tube 308 removes the flexible tubing used to connect the cannula to the vacuum means from the area of operation.

Also referring to FIG. 5, four-way servovalve 309 is shown connected to cylinder ports 310 and 311. Although the use of a single four-way valve 309 is shown with double-acting cylinder 305, it is also possible to use two three-way valves to control the operation of cylinder 305.

As discussed, an object of the present invention is to reduce physician fatigue during liposuction procedures. Automation of cannula motion alone, however, does not completely relieve the physician of all exertion. The physician must still supply the force required to counteract the reactionary force resulting from the driving of the cannula. It is therefore desirable to minimize or eliminate completely the reactionary force.

A preferred method of substantially minimizing reactionary force is to provide the system with one or more slave cylinders which do not actively participate in the driving of the cannula, but operate in an opposing manner to the drive cylinder or cylinders to counteract the reactive force produced by the drive cylinder or cylinders. Preferably, the system is configured to minimize or eliminate both axial reactionary forces and torque.

Figure 7:
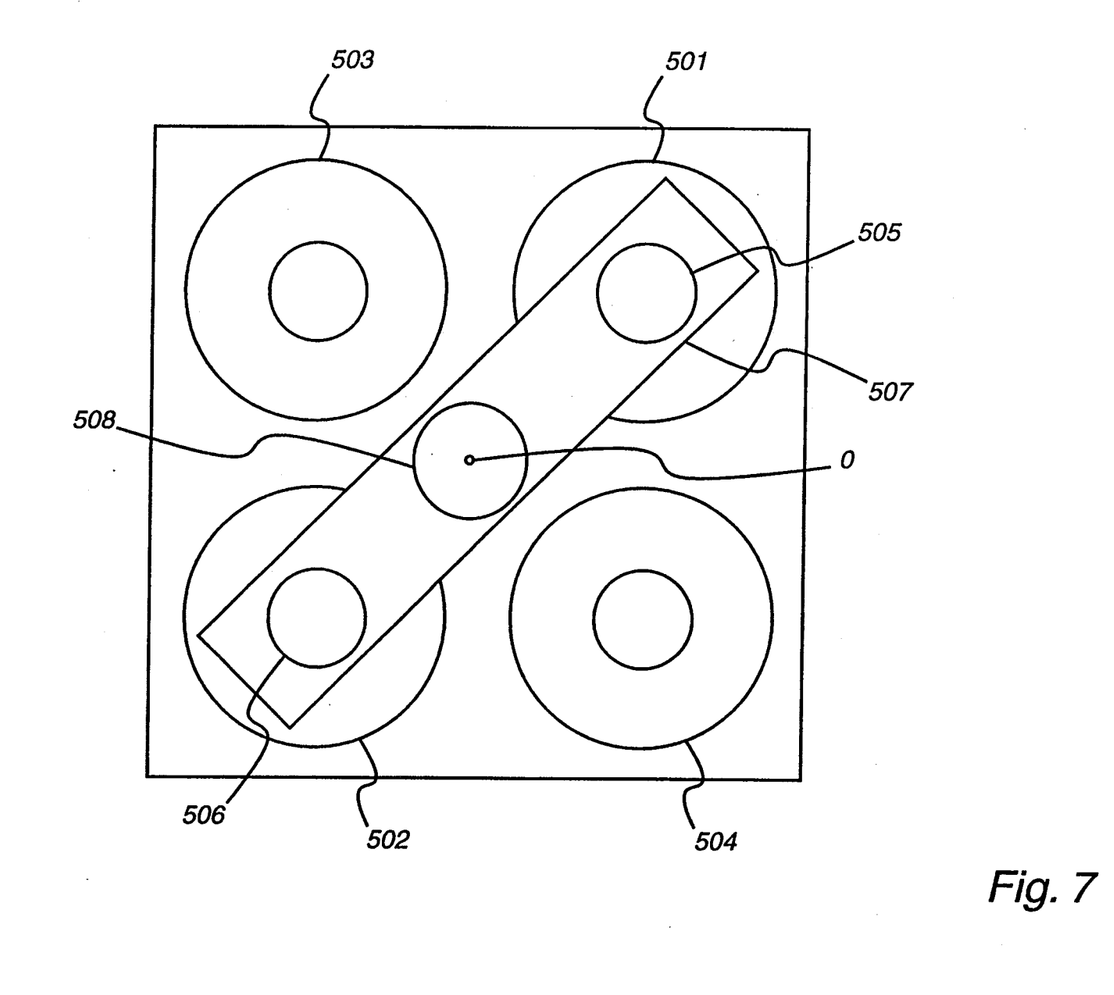
FIG. 7 is a frontal view of an embodiment of the present invention in which slave cylinders are used to counteract the reactionary force produced by the reciprocal, retrolinear motion of the cannula.

A preferred embodiment incorporating slave cylinders is shown in a frontal view in FIG. 7. In this embodiment, there are two drive cylinders, 501 and 502, and two slave cylinders, 503 and 504. Rods 505 and 506 of drive cylinders 501 and 502, respectively, are attached to cannula attachment means 507 to drive cannula 508. When a certain pressure is applied to drive cylinders 501 and 502 to drive cannula attachment means 502 forward, an equivalent counteractive force is applied to slave cylinders 503 and 504 to drive the pistons of those cylinders in the reverse direction. Thus, the resultant axial force on device 500 is minimized or completely eliminated. The symmetrical design illustrated in FIG. 6 also substantially minimizes or eliminates torque on device 500 by minimizing or eliminating any moment about axial center O.

Figure 8:
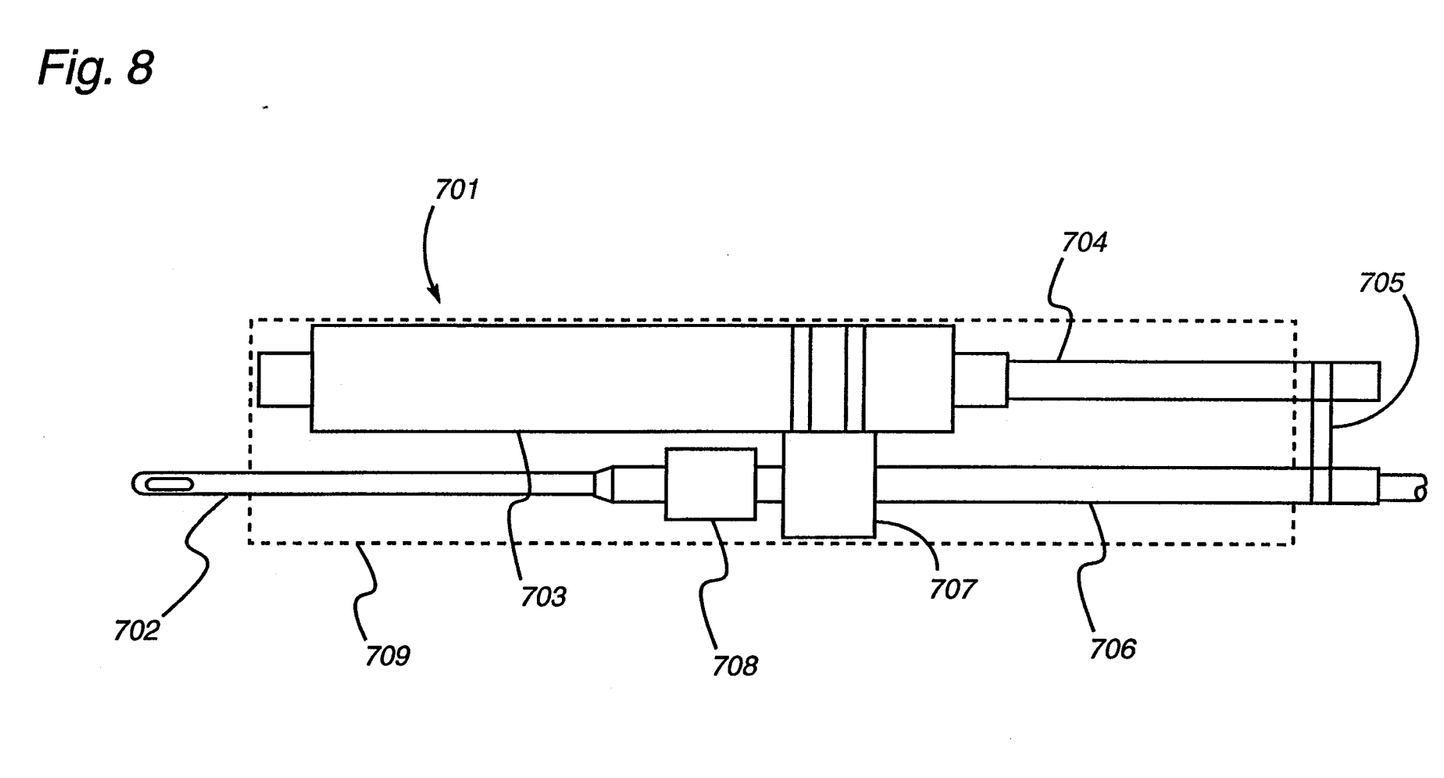
FIG. 8 is a side view of an embodiment of the present invention showing attachment of the cannula to minimize the distance from the operator's hand to the cannula tip.

Referring to FIG. 8, to enable the operator to maintain better control over automated device 701, cannula 702 is preferably attached to power means 703 so that the distance from the operator's hand to the tip of cannula 702 is minimized upon a full forward stroke of cannula 702. As illustrated in FIG. 8, this result may be accomplished by attaching cannula 702 to rod 704 of cylinder 703 at the rear of device 701 via attachment means 705.

In the embodiment of FIG. 8, guide rod 706 is slideably disposed within guide block 707 which is securely attached to cylinder 703. Cannula 702 is securely attached to guide rod 706 via cannula attachment means 708. Device 701 is provided also with a handle means 709 for gripping by the operator. In the embodiment of FIG. 7, handle means 709 is shown in dashed lines to be a cylindrical encasement enclosing both cylinder 703 and retracted cannula 702.

Automation of the rectilinear motion required for liposuction thus provides a means to greatly reduce physician fatigue while increasing control of cannula motion to provide better aesthetic results and less patient trauma.

In addition to the control of variables associated with cannula motion, an automated liposuction device preferably includes a means for actively controlling the vacuum pressure used in withdrawing the lipid material. Referring to FIG. 3, for example, the amount of fat removed from a given area can be controlled by appropriate adjustment of cannula velocity and/or vacuum pressure. By providing greater vacuum pressure within distal aspect D relative to central aspect C, one may effectively remove a more even distribution of fat over the entire radial pattern.

Controlled automation of liposuction procedures provides further advantages in that, the biological material being removed from the patient can be monitored and feedback provided to processing unit 20 so that the cannula motion and/or vacuum pressure can be altered in response to the observed nature of the removed biological materials. Under current procedures, the operating physician visually observes the nature of the removed lipids to monitor for occurrences such as excess blood content.

In FIG. 1, it is shown that automated liposuction device 1 is preferably provided with a monitoring means 23 which can optically, chemically or otherwise monitor the constitution and flow rate of material removed from the patient to determine, among other things, the blood content of the material. An example of a suitable monitoring means 23 for use in the present invention is the LM3000 General Aspirator Monitor available from MD Engineering Highland Company. As shown in FIG. 1, monitoring means 23 is in operative connection with tubing 24 which is connected to cannula nozzle 22. The data collected by monitoring means 23 is supplied to microprocessor 20 and the cannula motion and/or vacuum pressure is altered in an appropriate manner.

Device 1 also can be provided with a supply means through which fluids can be introduced during operation. It is currently common practice to provide irrigation during liposuction. The supply means can be used to supply lipolytic or hemostatic fluids to the patient's tissue. Preferably, such fluids are supplied to the area near the tip of cannula 2 where the apertures through which biological materials pass are located. The fluids can be supplied via a supply means such as a supply tube located within cannula 2 or adjacent cannula 2. Once again the flow rate and constitution of removed materials can be monitored via monitoring means 23 to provide feedback to microprocessor 20 to appropriately control the provision of such fluids.

Existing procedures for preparing the patient for lipectomy may be used in operations employing the present invention. The regions to be suctioned should be demarcated depending upon the technique to be used. Anesthesia can be general, peridural, or local. The patient should be in either the prone or supine position depending on the area to be targeted. A saline or dilute lidocaine with epinepherin solution may be infiltrated in the fatty deposits.

The incision is made in the skin from 5 to 15 mm. in length depending on the diameter of the cannula to be used. The cannula is then inserted into the incision creating a tunnel at the deep level of the tissue, near the fascia. This is necessary to avoid the lymphatics contained in the subcutaneous fat, and to retain skin trophicity and tonicity. The vacuum source is then activated at a negative pressure depending upon the size of the cannula.

Figure 9:
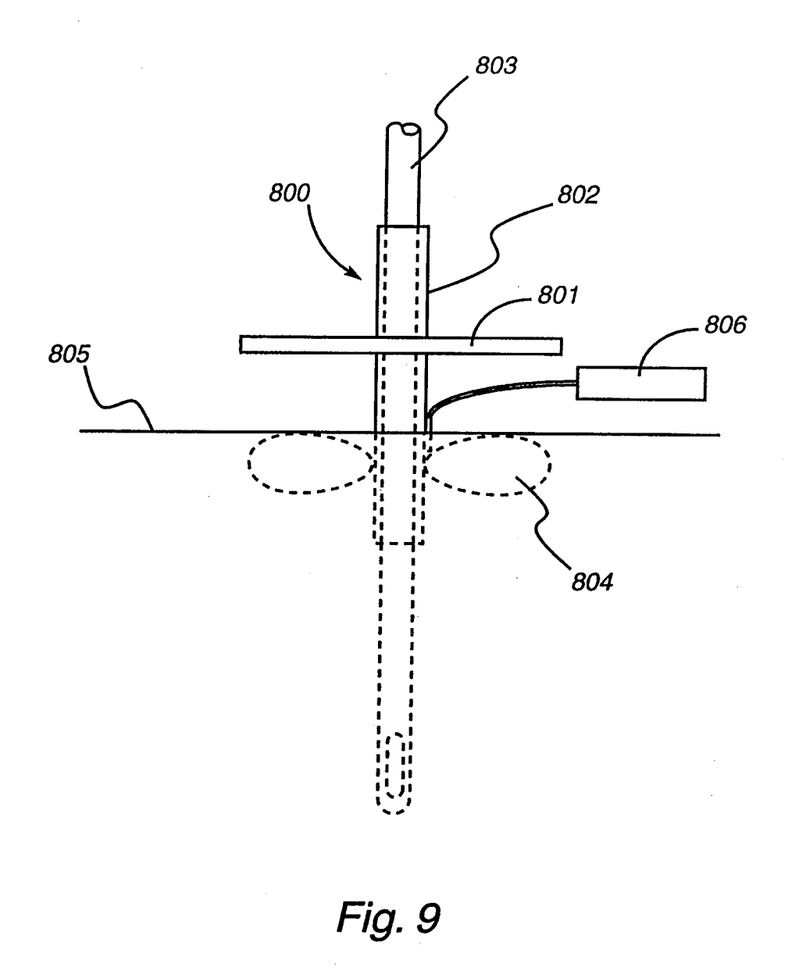
FIG. 9 is side of a protective sheath for use during liposuction.
Figure 10:
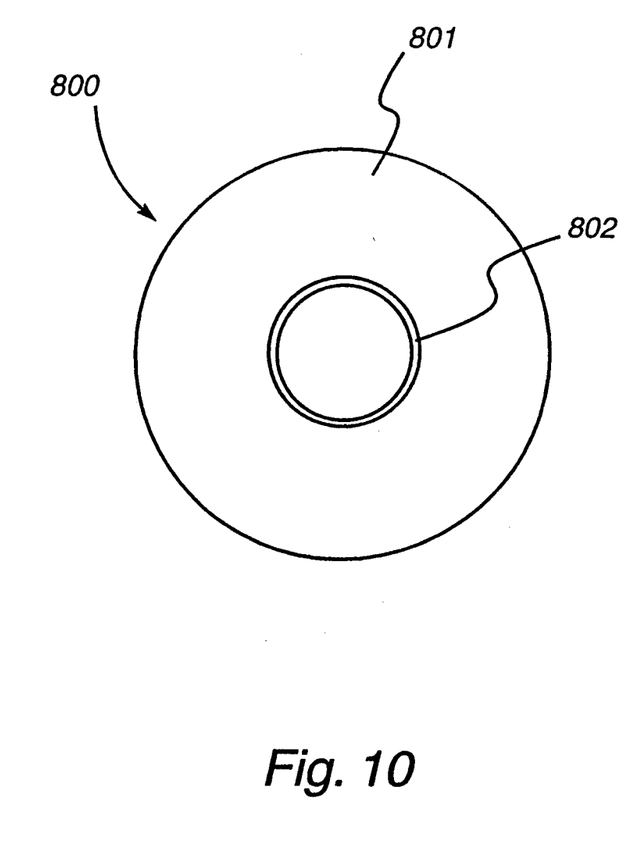
FIG. 10 is a top view of a protective sheath for use during liposuction.

Preferably the cannula is inserted into an incision through a protective sheath. An illustration of a protective sheath 800 is shown in FIG. 9 and 10. Protective sheath 800 comprises an exterior abutment means 801 connected to a protective element 802 at one end thereof. Protective element 802 is preferably substantially cylindrical in shape and of a diameter sufficient to allow cannula 803 to pass therethrough. Protector element 802 is preferably fabricated of a resilient material to prevent tearing but is sufficiently pliable to move with cannula 803. Certain polymeric materials are well suited for fabrication of protective element 802. An example of a suitable material is silicone rubber. Protective sheath 800 also comprises an expandable internal abutment means 804 placed beneath skin surface 805. Expandable internal abutment means 804 and external abutment means 801 prevent protective sheath 800 from being dislodged during the respective reciprocal motion of cannula 803. External abutment means 801 and expandable internal abutment means 804 may be pivotally connected to protective element 802 to facilitate angular movement of protective element 802 with angular movement of cannula 803.

In use, protective sheath 800 is inserted into incision 805 with expandable interior abutment means 804 in an unexpanded state to allow easy insertion. After insertion of protective sheath 800 into an incision (not shown) in skin surface 805, interior abutment means 804 is expanded to prevent the "pulling out" of protective sheath 800. Protective sheath 800 is preferably provided with expansion means 806 for expanding interior abutment means 804. In a preferred embodiment, expandable interior phalange comprises an inflatable bladder. In such an embodiment, expansion means 806 may be a syringe. Protective sheath 800 protects the skin 805 from the repetitive reciprocal motion of cannula 803.

The afforded protection reduces patient trauma and improves healing to achieve a more favorable aesthetic result.

When the cannula is in place, the operator can activate the automated reciprocal, rectilinear motion of the cannula by using a foot pedal or alternatively a control mechanism on the handle of the apparatus. The cannula motion variables, including the stroke length, force, rate and symmetry can be controlled via the control mechanism.

The operator should then begin to gently massage the region in which liposuction is being performed. The aspirated fat will be seen in the discharge hose. Fat is pure yellow, and if blood appears in the tubing the operator should change the orientation of the cannula, or remove it. As described above, the amount of biological material removed as well as its compositional nature are preferably monitored via monitoring means 23. After an adequate amount of fat has been removed, a new tunnel should be made and the procedure repeated.

When the removal is complete, compression bandages should be applied. More than one operation may be needed. Skin retraction may follow.

Although the invention has been described with reference to certain embodiments, this description is not meant to be construed in a limiting sense. Various modifications of the disclosed embodiments, as well as alternative embodiments of the invention, will become apparent to persons skilled in the art upon reference to the description of the invention. It is therefore contemplated that the appended claims will cover such modifications that fall within the true scope of the invention.

What is claimed is:

1. An automated device for performing suction lipectomy comprising:
   (a) a cannula;
   (b) a powered means for producing a reciprocal, rectilinear motion of the cannula, said motion being of a stroke length of at least 1 cm.;
   (c) a means for operatively connecting the cannula to said means for producing a reciprocal, rectilinear motion; and
   (d) a control means in operative connection with said powered means for maintaining active control over the reciprocal, rectilinear motion produced by the powered means, said control means comprising means for providing a control signal to said powered means responsive to input from the group consisting of a predetermined waveform and feedback from operation of said cannula, said control means being operable to control the reciprocal, rectilinear motion in a desired manner via the control signal provided to said powered means.

2. A device according to claim 1 further comprising means for controlling the stroke length of the cannula.

3. A device according to claim 2 wherein said means for controlling the stroke length comprises mechanical abutment means which are variable in position.

4. A device according to claim 2 wherein said means for controlling the stroke length comprises switch means appropriately located to control the stroke length.

5. A device according to claim 4 wherein said switch means are variable in position.

6. A device according to claim 1 further comprising a means for sensing force exerted upon the cannula by said power means.

7. A device according to claim 6 further comprising a means for warning an operator when the force exerted upon the cannula exceeds a predetermined threshold value, said warning means being in operative connection with said means for sensing cannula force.

8. A device according to claim 6 further comprising a means for ceasing powered operation of said powered means when the force exerted upon the cannula exceeds a predetermined threshold value, said means for ceasing powered operation being in operative connection with said control means.

9. A device according to claim further comprising a means for substantially restricting tangential, rotational motion of the cannula.

10. A device according to claim 1 further including a means for substantially counteracting reactionary force created by the motion of the cannula.

11. A device according to claim 1 wherein said control means further comprises a microprocessor.

12. A device according to claim 1 wherein said control means further comprises a servomechanism.

13. A device according to claim 1 wherein at least one electric motor is used as the powered means for producing the reciprocal, rectilinear motion.

14. A device according to claim 1 wherein at least one hydraulic actuator is used as the powered means for producing the reciprocal, rectilinear motion.

15. A device according to claim 1 wherein at least one pneumatic cylinder is used as the powered means for producing the reciprocal, rectilinear motion.

16. A device according to claim 15 wherein said pneumatic cylinder is a single-acting pneumatic cylinder.

17. A device according to claim 15 wherein said pneumatic cylinder is a double-acting pneumatic cylinder.

18. A device according to claim 15 further comprising means for controlling the stroke length of the cannula.

19. A device according to claim 18 wherein said means for controlling the stroke length comprises mechanical abutment means which are variable in position.

20. A device according to claim 18 wherein said means for controlling the stroke length comprises switch means appropriately located to control the stroke length.

21. A device according to claim 20 wherein said switch means are variable in position.

22. A device according to claim 15 further comprising a means for substantially restricting the tangential, rotational motion of the cannula.

23. A device according to claim 22 wherein said means for restricting the tangential, rotational motion of the cannula comprises pneumatic cylinder rod having a non-circular cross section.

24. A device according to claim 23 wherein said rod has a hexagonal cross section.

25. A device according to claim 22 wherein said means for restricting the tangential, rotational motion of the cannula comprises a guide means external to said pneumatic cylinder.

26. A device according to claim 15 wherein tangential, rotational motion of the cannula is restricted by attaching the cannula to more than one pneumatic cylinder.

27. A device according to claim 15 further including a means for substantially counteracting reactionary force created by the reciprocal, rectilinear motion.

28. A device according to claim 27 wherein said counteracting means comprises a least one slave cylinder operating in opposition to at least one pneumatic cylinder powering the reciprocal, rectilinear motion.

29. A device according to claim 15 further comprising a means for maintaining active control over the reciprocal, rectilinear motion produced by said at least one pneumatic cylinder.

30. A device according to claim 29 wherein said active control means comprises at least one servovalve.

31. A device according to claim 15 further comprising a means for maintaining active control over vacuum pressure supplied to the cannula.

32. A device according to claim 31 wherein said vacuum control means comprises a microprocessor.

33. The device of claim 15 further comprising a means of supplying a fluid to an area in the vicinity of an aperture of the cannula.

34. The device of claim 33 wherein said fluid comprises a component selected from the group consisting of lypolitic fluid and hemostatic fluid.

35. The device according to claim 15 further comprising a means for monitoring the constitution and flow rate of biological material removed during suction lipectomy, said monitoring means being in operative connection with said control means.

36. The device according to claim 35 wherein active control is maintained over said device according to data received from said monitoring means.

37. A device according to claim 1 further comprising a means for maintaining active control over vacuum pressure supplied to the cannula.

38. A device according to claim 37 wherein said vacuum control means comprises a microprocessor.

39. The device according to claim 37 further comprising a means for monitoring the constitution lipectomy, said monitor means being in operative connection and flow rate of biological material removed during suction lipectomy, said monitoring means being in operative connection with said control means.

40. The device according to claim 39 wherein active control is maintained over vacuum pressure according to data received from said monitoring means.

41. The device of claim 1 further comprising a means of supplying a fluid to an area in the vicinity of an aperture of the cannula.

42. The device of claim 41 wherein said fluid comprises a component selected from the group consisting of lypolitic fluid and hemostatic fluid.

43. The device of claim 1 further comprising a means for monitoring the constitution and flow rate of biological material removed during suction lipectomy, said monitoring means being in operative connection with said control means.

44. The device according to claim 43 wherein active control is maintained over said device according to data received from said monitoring means.

45. A device according to claim 1 further comprising a handle means.

46. A device according to claim 45 wherein said handle means is in operative attachment with the cannula to substantially minimize the distance between an operator's hand and a distal end of the cannula when the cannula is in a fully extended position.

47. An automated device for performing suction lipectomy comprising:
  (a) a cannula;
  (b) a powered means including at least one pneumatic cylinder for producing a reciprocal, rectilinear motion of the cannula, said motion being of a stroke length of at least 1 cm.;
  (c) a means for operatively connecting the cannula to said means for producing a reciprocal, rectilinear motion;
  (d) a control means in operative connection with said powered means for maintaining active control over the reciprocal, rectilinear motion produced by the powered means, said control means being operable to control the reciprocal, rectilinear motion in a desired manner via a control signal provided to said powered means; and
  (e) a means for sensing cannula force, said sensing means comprising a means for measuring the pressure within said pneumatic cylinder, said pressure measuring means being in operative connection with said control means.

48. A device according to claim 47 wherein said pressure measuring means is a pressure transducer.

49. An automated device for performing suction lipectomy comprising:
  (a) a cannula;
  (b) a powered means for producing a reciprocal, rectilinear motion of the cannula, said motion being of a stroke length of at least 1 cm., said powered means comprising at least one pneumatic cylinder;
  (c) a means for operatively connecting the cannula to said means for producing a reciprocal, rectilinear motion;
  (d) a control means in operative connection with said pneumatic cylinder for maintaining active control over the reciprocal, rectilinear motion produced by the at least one pneumatic cylinder; said control means comprising a microprocessor.

50. A device according to claim 49 further comprising at least one servovalve in operative connection with said microprocessor.

51. An automated device for performing suction lipectomy comprising:
  (a) a cannula;
  (b) a powered means for producing a reciprocal, rectilinear motion of the cannula, said motion being of a stroke length of at least 1 cm.;
  (c) a means for operatively connecting the cannula to said means for producing a reciprocal, rectilinear motion; and
  (d) a microprocessor for maintaining active control over the reciprocal, rectilinear motion produced by the powered means, said microprocessor controlling a servomechanism in a desired manner by providing a control signal to said servomechanism.

52. A automated device for performing suction lipectomy comprising:
  (a) a cannula;
  (b) a powered means including at least one pneumatic cylinder for producing a reciprocal, rectilinear motion of the cannula, said motion being of a stroke length of at least 1 cm.;
  (c) a means for operatively connecting the cannula to said means for producing a reciprocal, rectilinear motion;
  (d) a control means in operative connection with said powered means for maintaining active control over the reciprocal, rectilinear motion produced by the powered means, said control means being operable to control the reciprocal, rectilinear motion in a desired manner via a control signal provided to said powered means; and (e) switch means appropriately located for controlling the stroke length of the cannula, said switch means comprising magnetic reed switches disposed upon said pneumatic cylinder.

53. An automated device for performing suction lipectomy comprising:
   (a) a cannula;
   (b) a powered means including at least one pneumatic cylinder for producing a reciprocal, rectilinear motion of the cannula, said motion being of a stroke length of at least 1 cm.;
   (c) a means for operatively connecting the cannula to said means for producing a reciprocal, rectilinear motion;
   (d) a control means in operative connection with said powered means for maintaining active control over the reciprocal, rectilinear motion produced by the powered means, said control means being operable to control the reciprocal, rectilinear motion in a desired manner via a control signal provided to said powered means; and
   (e) a means for sensing cannula force, said sensing means being selected from the group consisting of cantilevered sensors, strain gauges and load cells, said sensing means being in operative connection with said control means.

54. An automated device for performing suction lipectomy comprising:
   (a) a cannula;
   (b) a powered means including at least one pneumatic cylinder for producing a reciprocal, rectilinear motion of the cannula, said motion being of a stroke length of at least 1 cm.;
   (c) a means for operatively connecting the cannula to said means for producing a reciprocal, rectilinear motion;
   (d) a control means in operative connection with said powered means for maintaining active control over the reciprocal, rectilinear motion produced by the powered means, said control means being operable to control the reciprocal, rectilinear motion in a desired manner via a control signal provided to said powered means;
   (e) a means for sensing force exerted upon said cannula by said powered means, said means for sensing cannula force being in operative connection with said control means; and
   (f) a means for ceasing powered operation of said powered means when cannula force exceeds a predetermined threshold value, said means for ceasing powered operation being in operative connection with said means for sensing cannula force.

55. An automated system for performing suction lipectomy comprising:
   (a) a cannula;
   (b) a powered means for producing a reciprocal, rectilinear motion of the cannula, said motion being of a stroke length of at least 1 cm.;
   (c) a means for operatively connecting the cannula to said means for producing a reciprocal, rectilinear motion;
   (d) a control means in operative connection with said powered means for maintaining active control over the reciprocal, rectilinear motion produced by the powered means, said control means comprising means for providing a control signal to said powered means responsive to input from the group consisting of a predetermined waveform and feedback resulting from operation of said cannula, said control means being operable to control the reciprocal, rectilinear motion in a desired manner via the control signal provided to said powered means; and
   (e) a protective sheath through which the cannula may pass to protect skin surrounding an incision.

56. A system according to claim 55 wherein said protective sheath comprises:
   (a) a protective element, said protective element formed with a passage therethrough to allow the cannula to pass therethrough;
   (b) an external abutment means attached to said protective element; and
   (c) an expandable internal abutment means attached to said protective element.

57. The system of claim 56 wherein said expandable internal abutment means comprises an inflatable bladder.

58. The system of claim 56 wherein said external abutment means is pivotally attached to said protective element.

59. The system of claim 56 wherein said expandable internal abutment means is pivotally attached to said protective element.

60. A device according to claim 55 further comprising a handle means.

61. A device according to claim 60 wherein said handle means is in operative attachment with the cannula to substantially minimize the distance between an operator's hand and a distal end of the cannula when the cannula is in a fully extended position.

62. An automated device for performing suction lipectomy comprising:
   (a) a cannula;
   (b) a powered means including at least one pneumatic cylinder for producing a reciprocal, rectilinear motion of the cannula, said motion being of a stroke length of at least 1 cm;
   (c) a means for operatively connecting the cannula to said means for producing a reciprocal, rectilinear motion;
   (d) a control means in operative connection, with said powered means for maintaining active control over the reciprocal, rectilinear motion produced by the powered means, said control means being operable to control the reciprocal, rectilinear motion in a desired manner via a control signal provided to said powered means; and
   (e) a means for sensing force exerted upon said cannula by said powered means, said sensing means being in operative connection with said control means.

63. A device according to claim 62 further comprising a means for warning an operator when said force exerted upon said cannula by said powered means exceeds a predetermined threshold valve.

* * * * *